United States Patent [19]

O'Reilly et al.

[11] Patent Number: 4,960,938
[45] Date of Patent: Oct. 2, 1990

[54] PREPARING 2-CHLOROBENZYLAMINE FROM 2-CHLOROBENZYLCHLORIDE VIA 2-CHLOROBENZYLPHTHALIMIDE

[75] Inventors: Neil J. O'Reilly, Grand Island; Stanley A. Sojka, Buffalo; Henry C. Lin, Grand Island, all of N.Y.

[73] Assignee: Occidental Chemical Corporation, Niagara Falls, N.Y.

[21] Appl. No.: 265,979

[22] Filed: Nov. 2, 1988

[51] Int. Cl.$^5$ .............................................. C07C 211/27
[52] U.S. Cl. ..................................... 564/366; 564/336
[58] Field of Search .................................. 564/366, 377

[56] References Cited

U.S. PATENT DOCUMENTS 4,038,412  7/1977  Grisar et al. ......................... 568/331
4,220,654  9/1980  Bolhofer et al. ..................... 548/336

OTHER PUBLICATIONS

Surrey, named Reactions in Organic Chemistry, 1954, pp. 79–80.
Solomons, Organic Chemistry, (Second Edition), 1980, pp. 777–779, 813–814.
Ergozhin et al., Linear and Crosslinked . . . , Chem. Abs., 99(22):176406v.

Primary Examiner—Glennon H. Hollrah
Assistant Examiner—Susan P. Treanor
Attorney, Agent, or Firm—James F. Tao; Arthur S. Cookfair; James F. Mudd

[57] ABSTRACT

2-Chlorobenzylamine is prepared from 2-chlorobenzylchloride in a two-step process. In the first step, 2-chlorobenzylchloride is reacted with alkali metal phthalimide, preferably formed in situ from potassium carbonate and phthalimide, to form the novel intermediate 2-chlorobenzylphthalimide. In the second step, the phthalimide ring of the 2-chlorobenzylphthalimide is cleaved to form 2-chlorobenzylamine. The first step is preferably carried out in an unreactive solvent at 60° C. to reflux temperature, for example, for 1 to 10 hours. The solvent is very preferably dimethylformamide which is advantageously recovered and used again as solvent in the conversion of 2-chlorobenzylchloride to 2-chlorobenzylphthalimide. The second step consists essentially, for example, of hydrazinolysis or hydrolysis. When the second step consists essentially of hydrazinolysis, the 2-chlorobenzylphthalimide is reacted with hydrazine to form 2-chlorobenzylamine and phthalylhydrazide, and the 2-chlorobenzylamine is separated by reacting with acid to form soluble amine salt, filtering out the phthalylhydrazide and then reacting the amine salt with base to convert it to the free amine. When the second step consists essentially of hydrolysis, the hydrolysis can be carried out in one step with alkali metal hydroxide or inorganic acid or in two steps, for example, with hydrolysis with alkali metal hydroxide followed by hydrolysis with inorganic acid. The hydrolysis is suitably carried out at temperatures of 60° C. to reflux temperature utilizing base and acid strengths ranging from 5% to saturated. Preferred hyrdolyzing agents are 40–60% aqueous KOH for one step base hydrolysis, 40–60% aqueous sulfuric acid for one step acid hydrolysis and 10–30% aqueous KOH followed by a mixture of water and concentrated HCl in a volume ratio ranging from 0.5:1 to 2:1 for the two-step base/acid hydrolysis. A second step consisting essentially of hydrolysis is preferred over a second step consisting essentially of hydrazinolysis not only for safety reasons but also because phthalic acid or a mixture of this with 2-chlorobeznylphthalamic acid can be recovered as by-product or by-product derivative which, contrary to the hydrazinolysis by product, phthalylhydrazide, are readily, respectively, converted to phthalimide and 2-chlorobenzylphthalimide by reaction with concentrated aqueous ammonium hydroxide. The phthalimide is useful in the in situ reaction in the first step to form 2-chlorobenzylphthal-imide. 2-Chlorobenzylphthalimide which is introduced with phthalimide into said first step becomes part of the product of the first step.

14 Claims, No Drawings

PREPARING 2-CHLOROBENZYLAMINE FROM 2-CHLOROBENZYLCHLORIDE VIA 2-CHLOROBENZYLPHTHALIMIDE

TECHNICAL FIELD

This invention is directed at a novel method for preparing 2-chlorobenzylamine from 2-chlorobenzylchloride and at a novel intermediate used in such preparation, namely 2-chlorobenzylphthalimide.

BACKGROUND OF THE INVENTION

2-Chlorobenzylchloride is commercially available and uses for it are being sought. Consideration has been given to converting it to 2-chlorobenzylamine which is useful for making thieno-pyridine derivatives including ticlopidine, a platelet inhibitor, as disclosed in Braye U.S. Pat. No. 4,127,580 (see compound 10 in Table 1 of U.S. Pat. No. 4,127,580). However, the literature discloses only methods for converting 2-chlorobenzylchloride to 2-chlorobenzylamine which have serious drawbacks. For example, Vassilev, G. N. et al, Dokl. Bolg. Akad. Nauk., 28, No. 1, pages 931–933, disclose reacting 2-chlorobenzylchloride with liquid $NH_3$ to form 2-chlorobenzylamine. This reaction requires a large excess of ammonia to minimize formation of secondary amine and also refrigeration to retain the ammonia in liquid state. Graymore, J. et al, J. Chem. Soc. (1945), pages 293–94 and Morley, J. S., J. Chem. Soc. (1961), pages 1414–16 disclose reacting 2-chlorobenzylchloride with hexamethylene to form a tetraamine quaternary derivative and then decomposing this to form 2-chlorobenzylamine. This reaction has the disadvantage of potentially producing carcinogenic bis(chloromethyl)ether as a by-product. Thus, a new route which does not require a large excess of reactant or refrigeration capacity and which does not produce such toxic by-products would be highly desirable.

SUMMARY OF THE INVENTION

It has been discovered herein that the disadvantages of the prior art can be avoided by utilizing a Gabriel synthesis to convert 2-chlorobenzylchloride to 2-chlorobenzylamine, i.e., by utilizing a method comprising the steps of (a) reacting the chloride with alkali metal phthalimide s that the alkali metal anion displaces the chloride to give 2-chlorobenzylphthalimide and (b) cleaving the phthalimide ring of 2-chlorobenzylphthalimide to form 2-chlorobenzylamine.

The first reaction step (i.e., step (a)) is essentially self-purifying and requires only washing to remove salt by-product. When dimethylformamide is utilized as a reaction solvent in this first step, it is readily recovered and recycled, i.e., used as a solvent again in a subsequent rendition of said first reaction step. When the second step, i.e., step (b), is carried out by hydrolysis, the by-product or a derivative of the by-product is phthalic acid or an admixture of this with 2-chlorobenzylphthalamic acid and these are readily converted, respectively, to phthalimide and 2-chlorobenzylphthalimide. The former is useful in the in situ preparation of alkali metal phthalimide in said first step and the latter is starting material for the second reaction step and if introduced into the first step with phthalimide becomes part of the product of the first reaction step.

DETAILED DESCRIPTION

Step (a), i.e., the reaction of 2-chlorobenzylchloride with alkali metal phthalimide to form 2-chlorobenzylphthalimide, can be carried out with no solvent or an unreactive solvent at a temperature ranging from about 60° C. to the reflux temperature of the reaction mixture. When the reaction is carried without solvent, the limiting temperature is the boiling point of 2-chlorobenzylchloride which at atmospheric pressure is about 220° C. When the reaction is carried out with solvent, the limiting temperature is the reflux temperature. The reaction is preferably carried out with stoichiometric quantities of reactants or a slight excess of alkali metal phthalimide.

The alkali metal phthalimide can be, for example, sodium phthalimide or potassium phthalimide and is preferably potassium phthalimide. The alkali metal phthalimide is preferably formed in situ in step (a) by reaction of phthalimide and the appropriate alkali metal carbonate, e.g., sodium carbonate or potassium carbonate. For this in situ formation, it is preferred to use stoichiometric quantities of phthalimide and carbonate or a slight excess of carbonate.

Phthalimide is readily obtained commercially or can be produced by any of several methods. For example, it can be produced by reacting phthalic acid or phthalic anhydride with urea (see Boehme et al U.S. Pat. No. 3,819,648 and CA Selects: Optimization of Organic Reactions, Issue 1, 1987, 106:4866e). It can also be prepared by reacting fused phthalic anhydride with gaseous ammonia in a heated reactor at 250–280° C. (CA 77:48070q) or by reacting phthalic anhydride and aqueous ammonia (Noyes et al, Organic Syntheses, Coll. Vol. I, Ed-In-Chief H. Gilman, 1932, pages 457–58). Preferably, it is formed from phthalic acid which is a by-product from step (b) herein or a derivative of by-product from step (b) herein. A very good method for converting phthalic acid to phthalimide which has not been found disclosed in the literature comprises reacting phthalic acid with a stoichiometric amount of aqueous ammonia, preferably concentrated aqueous ammonia, at a temperature ranging from room temperature to 300° C., for example, by heating gradually over a period of 0.5 to 2.5 hours from room temperature to 230–300° C., whereby product begins to sublime at 220–230° C. This reaction when applied to said phthalic acid by-product or said phthalic acid by-product derivative converts any 2-chlorobenzylphthalamic acid which may contaminate said phthalic acid by-product or by-product derivative to 2-chlorobenzylphthalimide which becomes part of the product of step (a). This use of by-product derivative from step (b) will be covered in additional detail later.

Step (a) preferably carried out in unreactive solvent, very preferably in dimethylformamide. Other very suitable solvents for the step (a) reaction include, for example, dimethylsulfoxide, 2-chlorotoluene, sulfolane, t-butanol and toluene.

Very preferably, step (a) comprises in situ formation of potassium phthalimide from phthalimide and potassium carbonate and comprises forming an admixture of 2-chlorobenzylchloride, phthalimide and potassium carbonate in dimethylformamide and reacting at a temperature ranging from 100° C. to 150° C. over a time period of 1 to 10 hours.

When step (a) is carried out in dimethylformamide, the resulting reaction mixture can be filtered to recover a mother liquor (filtrate) consisting essentially of dimethylformamide which can be used as a solvent in step (a) in a subsequent preparation according to the process herein.

We turn now to step (b), i.e., cleaving the phthalimide ring to form 2-chlorobenzylamine.

Step (b) consists essentially for example, of hydrazinolysis or hydrolysis.

When step (b) consists essentially of hydrazinolysis, the 2-chlorobenzylphthalimide intermediate produced in step (a) is reacted with hydrazine or hydrate thereof to form 2-chlorobenzylamine product and phthalylhydrazide by-product. This reaction is readily carried out with stoichiometric amounts of reactants or a slight excess of hydrazine in methanol or other alcohol solvent (e.g., ethanol or isopropanol) at 40° C. to the reflux temperature. Reaction at reflux temperature normally is completed in 1 to 10 hours. The product 2-chlorobenzylamine is readily separated from by-product phthalylhydrazide by removing alcohol solvent, e.g., by distilling, then adding aqueous inorganic acid (e.g., hydrochloric, sulfuric, or nitric acid) to form soluble acid salt of the amine, filtering out the insoluble phthalylhydrazide, then adding base, e.g., sodium hydroxide, to the filtrate to form the free amine which can be recovered by extraction, for example, utilizing methylene chloride or other appropriate solvent (e.g., diethyl ether, toluene, 2-chlorotoluene or ethyl acetate).

When step (b) consists essentially of hydrolysis, the hydrolysis can be carried out in a one-step base hydrolysis or a one-step acid hydrolysis or in a two-step acid/base or base/acid hydrolysis. A two-step hydrolysis with the first step being a base hydrolysis and the second step being an acid hydrolysis is preferred since the first carboxy nitrogen bond is readily cleaved by base hydrolysis but less readily cleaved by acid hydrolysis while the second carboxy nitrogen bond is readily cleaved by acid hydrolysis and less readily cleaved by base hydrolysis. Thus, the two-step hydrolysis involving first hydrolysis with base and then hydrolysis with acid enables use of lower concentration base and acid and/or shorter times than where only base or only acid is used for both cleavages.

Hydrolysis in step (b) is suitably carried out at temperatures of 60° C. to relfux using a stoichiometric amount or slight excess of aqueous base and/or acid at acid strengths of 5% to saturated and times of 15–100 hours such that cleavage of the first carboxy nitrogen bond occurs and at least in a major portion of the resulting 2-chlorobenzylphthalamic acid cleavage of the remaining nitrogen carboxy bond occurs. By-product phthalic acid and 2-chlorobenzylphthalamic acid is insoluble in acid solution and is readily removed from the reaction mixture by filtering. 2-Chlorobenzylamine product can be recovered from the basified filtrate by extraction using methylene chloride or other appropriate solvent (e.g., diethyl ether, toluene, 2-chlorotoluene or ethyl acetate).

For a preferred two-step hydrolysis, the first step is a base hydrolysis with KOH or NaOH (very, preferably with 10–30% aqueous KOH) under conditions to cleave the first nitrogen carboxy bond to form salt of 2-chlorobenzylphthalamic acid and the second step comprises adding to the reaction mixture resulting from the base hydrolysis step a mixture of water and concentrated HCl in a volume ratio ranging from 0.5:1 to 2:1 under conditions to cleave in a major portion of said salt the remaining nitrogen carboxy bond and to cause formation of insoluble by-product comprising phthalic acid in admixture with 2-chlorobenzylphthalamic acid which may be filtered to leave filtrate containing the product 2-chlorobenzylamine as its hydrochloride salt.

Preferred conditions for a one-step base hydrolysis for step (b) comprises utilizing 40–60% aqueous KOH at reflux temperature for a time period sufficient to cleave the first nitrogen carboxy bond and at least in a majority of cases the second.

The one-step base hydrolysis produces a by-product salts of phthalic acid (e.g., potassium phthalate) or a mixture of this with 2-chlorobenzylphthalamic salt (e.g., potassium 2-chlorobenzylphthalamate). The insoluble free acids are obtained from these, i.e., as by-product derivative, by acidification, e.g., with concentrated hydrochloric acid, and are readily filtered from the reaction mix, after extracting or separating the 2-chlorobenzylamine product.

When step (b) comprises a one-step acid hydrolysis, preferred conditions comprise utilizing 40–60% sulfuric acid at reflux temperature for a time period sufficient to cleave the first nitrogen carboxy bond and at least in a majority of the cases the second.

The one-step acid hydrolysis produces the acid salt of 2-chlorobenzylamine. The one-step acid hydrolysis produces as insoluble by-product phthalic acid or admixture of phthalic acid and 2-chlorobenzylphthalamic acid which can be removed from the reaction mix by filtering. The 2-chlorobenzylamine acid salt in the filtrate is readily converted to the free amine by the addition of base, e.g., NaOH.

A step (b) consisting essentially of hydrolysis is preferred over a step (b) consisting essentially of hydrazinolysis not only for safety reasons but also because phthalic acid or admixture of phthalic acid and 2-chlorobenzylphthalamic acid can be recovered as by-product or by-product derivative which, contrary to the hydrazinolysis by-product, phthalylhydrazide, are readily respectively converted by reaction with aqueous ammonium hydroxide as described above to phthalimide and an admixture of phthalimide and 2-chlorobenzylphthalimide which can be introduced into step (a) herein as the source of phthalimide reactant. Any 2-chlorobenzylphthalimide which is introduced into step (a) in admixture with phthalimide becomes part of the product of step (a).

The product of step (a) which is the intermediate in the method herein, namely 2-chlorobenzylphthalimide, is a novel compound. It is a white solid, mp 187–191° C.

The invention is illustrated in the specific example which follow.

EXAMPLE 1

160.0 g of phthalimide and 85.6 g of potassium carbonate were ground together and then added to a mechanically stirred mixture of 162.8 g of a 2-chlorobenzylchloride and 800 mL of dimethylformamide contained in a 2 L, 3-neck flask. The reaction mixture was then heated to 120° C. and stirred at that temperature for 4.5 hours. Evolution of carbon dioxide was noted as heating was begun. The flask was allowed to cool to 50° C. with stirring and was then placed in an ice/water bath and cooled to 10–15° C. The flask contents were filtered through a coarse glass frit and the mother liquor was saved for recycling. The collected solid was washed with 3×300 mL of water, sucked dry and then dried overnight in a vacuum oven. A melting point determination indicated the presence of inorganic salt.

The resulting product was, therefore, slurried in 1 L of water and stirred for 15 minutes, then filtered and washed with 2×500 mL of water. The product, a white solid, was dried at the pump and then in a vacuum oven overnight. The yield was 230.4 g (84.5%), of 2-chlorobenzylphthalimide, a white solid, mp 189-191° C. GC analysis (DB5 capillary) indicated the purity to be very high (≧99%).

When in Example 1, an equimolar amount of sodium carbonate is substituted for the potassium carbonate or an equimolar amount of potassium phthalimide or sodrium phthalimide is substituted for the phthalimide and potassium carbonate, good yields of 2-chlorobenzylphthalimide are also obtained.

EXAMPLE 2

A 1 L 3-neck flask was charged with 391 g of the mother liquor from Example 1 and 81.4 g of 2-chlorobenzylchloride. 80.0 g of phthalimide and 42.8 g of potassium carbonate were ground together and then added to the stirred reaction mixture. Stirring was continued and the flask was heated to 120° C. for 5 hours. Evolution of carbon dioxide was again observed as the heating was begun. The reaction mixture was allowed to cool overnight, and then cooled to 10-15° C. and filtered. The mother liquor was saved for recycling. The collected solid was slurried with 500 mL of water, filtered and then washed with 3×300 mL of water. The white solid was dried at the pump and then in a vacuum oven at 130° C. and 25" for 2 hours. The yield was 121.2 g (87%) of 2-chlorobenzylphthalimide, a white solid, mp 187-190° C. GC analysis (DB5 column) indicated purity to be ver high (≧99.4%).

The phthalimide used in Example 2 is readily made according to the following method. A 25 mL, round-bottomed, single-necked flask equipped with a Barrett trap and a condenser was charged with a 3.0 g of phthalic acid and a 2.7 mL of concentrated aqueous ammonia. The reaction mixture was then heated gradually to 280° C. over a period of 1.5 hours. An initial exotherm was observed when the ammonia was added, then water collected in the trap above 100° C. Finally the product began to sublime at 220-230° C. The solid product was collected from the sides of the flask and analyzed by GC and IR. A quantitative yield of phthalimide was obtained.

EXAMPLE 3

A 2 L, 3-neck flask was charged with 1 L of methanol, 121 g of 2-chlorobenzylphthalimide and 40 mL of 85% hydrazine hydrate. The reaction mixture was stirred mechanically and heated under reflux (65° C.) for 3 hours. The flask was allowed to cool slightly, and 200 mL of water was added. The flask was adapted for distillation and 800 mL of methanol wa distilled out. 400 mL of 50% V/V aqueous hydrochloric acid solution was then added dropwise. The reaction mixture was heated under reflux (85° C.) for 2 hours with stirring and was then allowed to cool overnight. The reaction mixture was filtered and the collected solid was washed with 5×200 mL of water. The collected solid was identified by IR spectroscopy to be phthalylhydrazide. The aqueous solution was rendered basic (pH 10-11) by the addition of sodium hydroxide pellets to the stirred, cooled solution. The oily liquid which came out of the solution was extracted with 5×200 mL of methylene chloride and the combined extracts were dried over anhydrous sodium sulfate. The sodium sulfate was filtered out and washed with 3×50 mL of methylene chloride. The wash solution was added to the combined extracts. Then solvent was removed using a rotary evaporator and the residue was distilled through a vacuum jacketed Vigreaux column.

The yield of pure (≧99.8% by DB5 capillary GC) 2-chlorobenzylamine was 56.17 g (88%), bp 84° C. (6 mm). High field $^1$H NMR spectroscopy did not indicate the presence of any impurities.

EXAMPLE 4

A 250 mL, round-bottomed, 3-necked flask was charged with 82.5 g of 20% aqueous potassium hydroxide and 20 g (73.6 mmol) of 2-chlorobenzylphthalimide. The reaction mixture was refluxed (bath temperature 130° C.) for 18.3 h with stirring, and then allowed to cool to room temperature. A mixture containing 50 mL of water and 50 mL of concentrated hydrochloric acid was then added dropwise and the reaction mixture was heated under reflux for a further 22.5 hours. The reaction mixture was then allowed to cool, and the cooled reaction mixture was filtered, and the collected solids were washed with 5×10 mL of water, and dried in a vacuum oven. NMR, IR and GC analysis indicated these to be mainly phthalic acid contaminated with 2-chlorobenzylphthalamic acid (11.2 g, 92%). The filtrate was rendered basic (pH 10) by the addition of potassium hydroxide pellets, and was then extracted with 4×100 mL of methylene chloride. After stripping of the solvent, a 98% yield (10.23 g) of 2-chlorobenzylamine was obtained (purity 99% by GC).

EXAMPLE 5

A 100 mL, round-bottomed, single-necked flask was charged with 20.0 g (73.6 mmol) of 2-chlorobenzylphthalimide and 82.5 g of 20% aqueous KOH solution (16.5 g KOH in 66 mL of water). The reaction mixture was heated under reflux for 48 hours (bath temperature 130° C.) with stirring, and then transferred to a separating funnel. The product was allowed to cool and then was extracted with 60 mL of methylene chloride, followed by 2×50 mL of diethyl ether. The extracts were combined, dried over anhydrous sodium sulfate, filtered, and the solvent was then stripped on a rotary evaporator. The yield of crude 2-chlorobenzylamine was 8.0 g (77%). The product was slightly yellow. Distillation under reduced pressure afforded substantially pure 2-chlorobenzylamine as a colorless liquid (7.7 g, 74%); bp 67-70° C. (5 mmHg). Acidification of the aqueous layer with hydrochloric acid to pH of approximately 1 caused the formation of a thick white precipitate which is indicated to be an admixture (4.95 g) of phthalic acid and 2-chlorobenzylphthalamic acid.

Solid by-product obtained from filtering (4.63 g) contained phthalic acid and 2-chlorobenzylphthalamic acid in a weight ratio of 7:3. This admixture was charged into a 25 mL, round-bottomed, single-necked flask equipped with a Barrett trap and a condenser, after which 3.71 g of concentrated aqueous ammonia was charged. The reaction mixture was heated gradually to 300° C. over a period of 1.5 hours. An initial exotherm was observed when the ammonia was charged; water collected in the trap above 100° C. and finally product consisting of phthalimide (72% by weight) and 2-chlorobenzylphthalimide (28% by weight) began to sublime. The solid product was collected from the sides of the flask and is used as the source of phthalimide in a preparation of 2-chlorobenzylphthalimide utilizing molar proportions and conditions the same as in Example 1. The 2-chlorobenzylphthalimide is hydrolyzed to 2-chlorobenzylamine utilizing molar proportions and conditions the same as above in this Example and substantially pure 2-chlorobenzylamine is recovered.

EXAMPLE 6

A 2 L, round-bottomed, 3-necked flask was charged with 830 g of 50% aqueous potassium hydroxide solution, and 333 g of 2-chlorobenzylphthalimide. The reaction mixture was then heated under reflux (pot temperature 125–128° C.) for 21 hours with stirring. It was then cooled in iced-water and allowed to settle in a separating funnel. The lower aqueous layer was drained, diluted with 2 L of water and acidified with 676 g of concentrated hydrochloric acid (with cooling). This caused the formation of a white precipitate, which was collected by filtration and dried in a vacuum oven overnight to yield 199.9 g of phthalic acid (98%). The organic layer was essentially pure (99.9% by GC) 2-chlorobenzylamine (163.4 g, 1.15 mol, 93.5%).

EXAMPLE 7

A 100 mL, round-bottomed, single-necked flask was charged with 0.90 g of 2-chlorobenzylphthalimide and 20 mL 50% sulfuric acid. The reaction mixture was refluxed for 25 hours, and then was cooled, filtered, and the collected solids were washed with 25 mL of water. Said collected solids were an admixture of phthalic acid and 2-chlorobenzylphthalamic acid. The filtrate was rendered basic by the addition of NaOH pellets, and then extracted with 3×30 mL of methylene chloride. The extracts were dried over anhydrous sodium sulfate, filtered, and stripped of solvent to obtain 2-chlorobenzylamine in 60% yield (0.28 g); purity 99.9% by GC and NMR.

COMPARATIVE EXAMPLE 1

When 2-chlorobenzylphthalimide was heated under reflux with a 1:1 mixture of concentrated hydrochloric acid and water for 3 hours, the starting material was recovered unchanged in 94% yield.

COMPARATIVE EXAMPLE 2

When 2-chlorobenzylphthalimide was heated under reflux with 1:1:1 mixture of concentrated hydrochloric acid, acetic acid, and water for 24.5 hours, the starting material was recovered unchanged in 97% yield.

Variations will be evident to those skilled in the art. Therefore, the scope of the invention is intended to be defined by the claims.

What is claimed is:

1. A method for preparing 2-chlorobenzylamine, said method comprising the steps of:
   (a) reacting 2-chlorobenzylchloride with alkali metal phthalimide at a temperature ranging from about 60° C. to the reflux temperature to form 2-chlorobenzylphthalimide, and
   (b) cleaving the phthalimide ring of 2-chlorobenzylphthalimide to form 2-chlorobenzylamine.

2. A method as recited in claim 1 wherein step (a) is carried out in an unreactive solvent and the alkali metal phthalimide is formed in situ from phthalimide and alkali metal carbonate and wherein step (b) consists essentially of hydrazinolysis or hydrolysis.

3. A method as recited in claim 2 wherein step (a) comprises in situ formation of potassium phthalimide from phthalimide and potassium carbonate and is carried out in dimethylformamide at a temperature ranging from 100° C. to 150° C. over a time period of 1 to 10 hours and wherein step (b) consists essentially of hydrolysis.

4. A method as recited in claim 3 wherein step (b) comprises a two-step hydrolysis wherein the first hydrolysis step is a base hydrolysis with KOH or NaOH and the second hydrolysis step is an acid hydrolysis with acid selected from the group consisting of hydrochloric, sulfuric acid nitric acids.

5. The method of claim 4 wherein the base hydrolysis is carried out with 10–30% aqueous KOH and the acid hydrolysis comprises adding to the reaction mixture resulting from base hydrolysis a mixture of water and concentrated HCl in a volume ratio ranging from 0.5:1 to 2:1 and wherein by-product is separated comprising phthalic acid admixed with 2-chlorobenzylphthalamic acid.

6. The method of claim 5 wherein said separated by-product admixture is reacted with ammonium hydroxide at a temperature ranging from room temperature to 300° C. to form admixture of phthalimide and 2-chlorobenzylphthalimide which is used in step (a) for the in situ preparation of alkali metal phthalimide reactant.

7. The method of claim 6 wherein mother liquor consisting essentially of dimethylformamide is recovered from step (a) by filtering and is used as solvent for the reaction of 2-chlorobenzylchloride with alkali metal phthalimide to form 2-chlorobenzylphthalimide.

8. The method of claim 3 wherein step (b) comprises a one-step base hydrolysis carried out utilizing aqueous sodium or potassium hydroxide at a strength of 5% to saturated at a temperature of 60° C. to reflux temperature.

9. The method of claim 8 wherein the one-step base hydrolysis is carried out utilizing 40–60% aqueous KOH at reflux temperature.

10. The method of claim 3 wherein step (b) comprises a one-step acid hydrolysis utilizing 40–60% sulfuric acid at reflux temperature.

11. The method of claim 2 wherein step (b) consists essentially of hydrazinolysis and comprise reacting 2-chlorobenzylphthalimide with hydrazine or hydrate thereof to form 2-chlorobenzylamine and phthalylhydrazide, and the 2-chlorobenzylamine is separated by reacting with acid to form soluble amine salt, filtering out the phthalylhydrazide and then reacting said amine salt with base to convert it to the free amine.

12. The method of claim 2 wherein step (b) consists essentially of hydrolysis and by-product or by-product derivative is phthalic acid or an admixture of phthalic acid and 2-chlorobenzylphthalamic acid and said by-product or by-product derivative is reacted with ammonium hydroxide at a temperature ranging from room temperature to 300° C. to respectively form phthalimide or an admixture of phthalimide and 2-chlorobenzylphthalimide.

13. The method of claim 12 wherein the resulting phthalimide or admixture of phthalimide and 2-chlorobenzylphthalimide is used as source of phthalimide for said in situ preparation of alkali metal phthalimide.

14. The method of claim 3, wherein mother liquor consisting essentially of dimethylformamide is recovered from step (a) by filtering and is used as solvent for the reaction of 2-chlorobenzylchloride with alkali metal phthalimide to form 2-chlorobenzylphthalimide.

* * * * *